(12) United States Patent
Lee et al.

(10) Patent No.: US 11,475,612 B2
(45) Date of Patent: Oct. 18, 2022

(54) DEVICE FOR SPATIAL NORMALIZATION OF MEDICAL IMAGE USING DEEP LEARNING AND METHOD THEREFOR

(71) Applicant: SEOUL NATIONAL UNIVERSITY R&DB FOUNDATION, Seoul (KR)

(72) Inventors: Dong Young Lee, Seoul (KR); Yu Kyeong Kim, Seoul (KR); Jae Sung Lee, Seoul (KR); Min Soo Byun, Seoul (KR); Seong A Shin, Seoul (KR); Seung Kwan Kang, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 161 days.

(21) Appl. No.: 16/965,815

(22) PCT Filed: Feb. 25, 2019

(86) PCT No.: PCT/KR2019/002264
§ 371 (c)(1),
(2) Date: Jul. 29, 2020

(87) PCT Pub. No.: WO2019/168310
PCT Pub. Date: Sep. 6, 2019

(65) Prior Publication Data
US 2021/0035341 A1    Feb. 4, 2021

(30) Foreign Application Priority Data

Feb. 28, 2018  (KR) .................. 10-2018-0024743
Oct. 16, 2018  (KR) .................. 10-2018-0123300

(51) Int. Cl.
*G06T 11/00*    (2006.01)
*G06T 7/00*    (2017.01)
(Continued)

(52) U.S. Cl.
CPC .......... *G06T 11/008* (2013.01); *A61B 5/055* (2013.01); *A61B 5/7221* (2013.01);
(Continued)

(58) Field of Classification Search
CPC .............. G06T 11/008; G06T 7/0014; G06T 2207/10088; G06T 2207/20081;
(Continued)

(56) References Cited

U.S. PATENT DOCUMENTS 7,856,137 B2 * 12/2010 Yonezawa ............ G06V 10/752
382/136
10,614,547 B2 *  4/2020 Lundqvist ............... G06T 7/337
(Continued)

FOREIGN PATENT DOCUMENTS

KR       101223681 B1    1/2013
KR      2014-0088840 A   7/2014
KR      2015-0036230 A   4/2015

OTHER PUBLICATIONS

Choi, H., et al., "Generation of Structural MRI mages from Amyloid PET: Application to MR-Less Quantification", Journal of Nuclear Medicine, vol. 59, Issue 7, Dec. 7, 2017, DOI: 10.2967/jnumed.117.199414, 30 pages. (Year: 2017).*
(Continued)

*Primary Examiner* — Van D Huynh
(74) *Attorney, Agent, or Firm* — Kilpatrick Townsend & Stockton LLP

(57) ABSTRACT

A device for spatially normalizing a medical image includes: an adaptive template generation unit configured such that when a plurality of functional medical images are input to a deep learning architecture, the adaptive template generation unit generates, based on prestored learning data, an adaptive template for spatially normalizing the plurality of functional medical images; a learning unit configured to learn by
(Continued)

repeating a process of generating an image from an input functional medical image of a user based on the adaptive template through a generative adversarial network (GAN) and determine authenticity of the generated image; and a spatial normalization unit configured to provide the functional medical image of the user which is spatially normalized based on results of the learning.

6 Claims, 9 Drawing Sheets

(51) Int. Cl.
*G06N 3/04* (2006.01)
*G06N 3/08* (2006.01)
*A61B 5/00* (2006.01)
*A61B 5/055* (2006.01)

(52) U.S. Cl.
CPC ......... *A61B 5/7246* (2013.01); *G06N 3/0454* (2013.01); *G06N 3/08* (2013.01); *G06T 7/0014* (2013.01); *G06T 2207/10088* (2013.01); *G06T 2207/20081* (2013.01); *G06T 2207/20084* (2013.01); *G06T 2207/30004* (2013.01)

(58) Field of Classification Search
CPC . G06T 2207/20084; G06T 2207/30004; G06T 2207/10081; G06T 2207/10104; G06T 2207/30016; G06T 7/30; G06T 7/0012; A61B 5/055; A61B 5/7221; A61B 5/7246; G06N 3/0454; G06N 3/08; G06N 3/088

USPC ........................................................ 382/131
See application file for complete search history.

(56) References Cited

U.S. PATENT DOCUMENTS

2014/0350392 A1* 11/2014 Lundqvist .............. A61B 6/037
600/425
2019/0228298 A1* 7/2019 Suzuki ..................... G06N 5/02
2020/0090350 A1* 3/2020 Cho ....................... G06T 7/0012

OTHER PUBLICATIONS

Fripp J. et. al., "Generative Atlases and Atlas Selection for C11-PIB PET-PET Registration of Elderly, Mild Cognitive Impaired and Alzheimer Disease Patients," Biomedical Imaging: From Nano to Macro, 2008. ISBI 2008. 5 International Symposium. May 14, 2008, pp. 1155-1158. (Year: 2008).*

International Search Report and Written Opinion mailed in International Patent Application No. PCT/KR2019/002264, filed Feb. 25, 2019, 9 pages.

Choi, H., et al., "Generation of Structural MR Images from Amyloid PET: Application to MR-Less Quantification", Journal of Nuclear Medicine, vol. 59, Issue 7, Dec. 7, 2017, DOI: 10.2967/jnumed.117.199414, 30 pages.

Notification of Reason for Refusal dated Feb. 21, 2020 in Korean Patent Application No. 20180123300, filed Oct. 16, 2018, 9 pages.

* cited by examiner

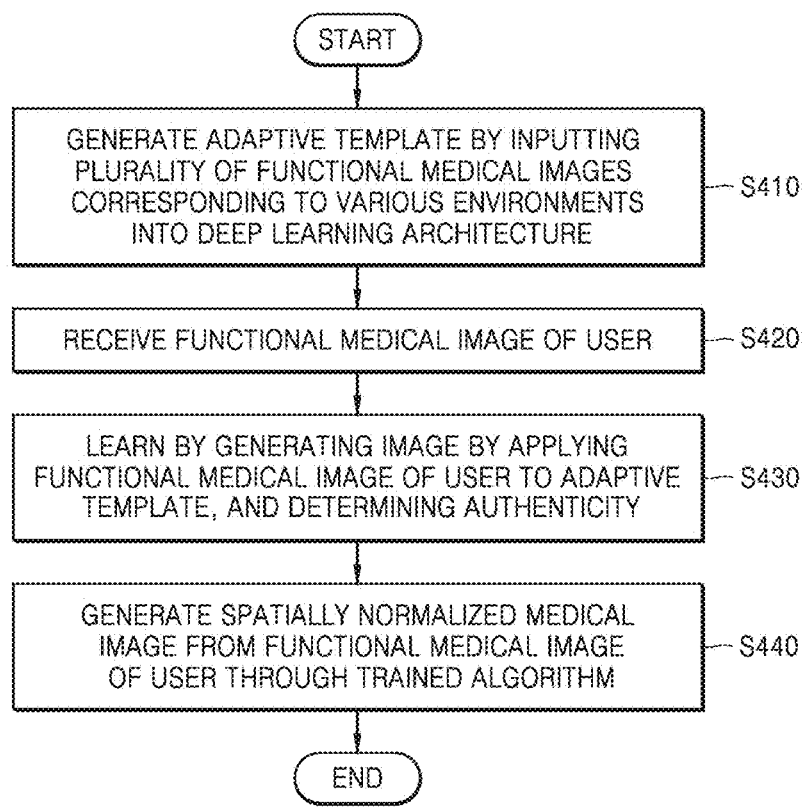

DEVICE FOR SPATIAL NORMALIZATION OF MEDICAL IMAGE USING DEEP LEARNING AND METHOD THEREFOR

TECHNICAL FIELD

Provided are a device for spatially normalizing a medical image through deep learning and a method used by the device.

BACKGROUND ART

For statistical analysis of medical images, it is recommendable to normalize images obtained from individual subjects into a single space and compare the 3D pixel values of the normalized images.

In particular, spatial normalization (SN or anatomical standardization) is an essential procedure in statistical comparison or objective evaluation of brain positron emission tomography (PET) images and single photon emission computed tomography (SPECT) images.

Many errors occur when spatial normalization (SN) is performed using only brain positron emission tomography (PET) images. Specifically, it is difficult to spatially normalize, using independent information, images obtained by a method such positron emission tomography (PET), single photon emission computed tomography (SPECT), functional magnetic resonance imaging (fMRI), electroencephalogram (EEG), or magnetoencephalography (MEG) because these images are functional images and have limited resolution.

Therefore, in general, magnetic resonance imaging (MRI) images or computed tomography (CT) images are captured together with functional images, and after the MRI or CT images are first spatially normalized to obtain a deformation vector field, the functional images are spatially normalized by applying the deformation vector field to the functional images.

This method is advantageous in obtaining accurate data, but incurs high costs because of use of expensive equipment, thereby causing limitations in time and cost.

In addition, there is a method of performing spatial normalization (SN) on brain positron emission tomography (PET) images by using an average template obtained from various samples. However, this method does not accurately reflect various features of images of patients, normal people, etc., and thus it is difficult to perform an accurate analysis.

Also, in recent years, research has been conducted using bigdata-based deep machine learning to successfully solve complex and high-level problems in many fields.

Therefore, there is a need for a technique for performing accurate spatial normalization based on machine learning at low costs and without having to additionally capture magnetic resonance imaging (MRI) images or computed tomography (CT) images.

DESCRIPTION OF EMBODIMENTS

Technical Problem

According to an embodiment of the present invention, a template which is individually adaptable is generated through deep learning, and a functional medical image is spatially normalized based on the template.

In addition, other problems which are not specifically mentioned may be solved.

Solution to Problem

According to an embodiment of the present disclosure, a device for spatially normalizing a medical image includes: an adaptive template generation unit configured such that when a plurality of functional medical images are input to a deep learning architecture, the adaptive template generation unit generates, based on prestored learning data, an adaptive template for spatially normalizing the plurality of functional medical images; a learning unit configured to learn by repeating a process of generating an image from an input functional medical image of a user based on the adaptive template through a generative adversarial network (GAN) and determining authenticity of the generated image; and a spatial normalization unit configured to provide the functional medical image of the user which is spatially normalized based on results of the learning.

The adaptive template generation unit may be further configured to measure a difference between an adaptive template result obtained from the deep learning architecture and an image spatially normalized based on MRI data which is the prestored learning data, and generate, through deep learning, an adaptive template which is individually adaptable for minimizing the measured difference.

The learning unit may be further configured to: generate a spatially normalized image by spatially normalizing the functional medical image of the user based on the adaptive template; determine authenticity of the spatially normalized image by comparing the spatially normalized image with an image spatially normalized based on MRI data which is the prestored learning data, and after generating results of the determining, repeat a process of generating and determining a spatially normalized image; and finish the learning when results of the determining show that the spatially normalized image is not distinguishable from the image spatially normalized based on the MRI data which is the prestored learning data.

The learning unit may be further configured to be repeatedly trained to minimize a Jensen-Shannon divergence between a data probability distribution of the spatially normalized image and a data probability distribution of normalized MRI.

The learning unit may be further configured to be repeatedly learn through a process of solving a min-max problem using the following expression:

where $$\min_{\theta_G}\max_{\theta_D} E_{x \sim Pdata(x)}[\log D(x)] + E_{z \sim PG(z)}[1 - \log D(G(z))] + 10^{-5} L_{GAN}^{fid}$$

$$L_{GAN}^{fid} = \sum_{i=0}^{m} \frac{(I_i^{MNI} - G(Z_i))^2}{\sum_{all\ voxels} I_i^{MNI}}$$

where D( ) refers to a generator which generates an image, G( ) refers to a discriminator which determines an image, z refers to a functional medical image in a native space, x refers to MRI-based SN results, $\theta_G$ and $\theta_D$ respectively refer to a parameter of the generator and a parameter of the discriminator, E refers to an expected value for a given probability distribution, $L_{GAN}^{fid}$ refers to fidelity loss between MRI-based SN results, m refers to a batch size, refers to an image indicating MRI-based SN results in an MNI space, and refers to a functional medical image in a basic space.

According to an embodiment of the present invention, there is provided a method used by a device for spatially normalizing a medical image, the method including: generating an adaptive template by applying a plurality of functional medical images corresponding to various environments to a deep learning architecture; learning by repeating a process of generating an image from an input functional medical image of a user based on the adaptive template through a generative adversarial network (GAN) and determining authenticity of the generated image; and after the learning, providing a spatially normalized functional medical image of the user based on results of the learning.

Advantageous Effects of Disclosure

According to an embodiment of the present invention, spatial normalization may be performed using an optimal template which is obtained from images by deep learning, and thus, highly accurate results may be obtained while minimizing errors.

In addition, since quantitative and statistical analysis is possible through normalization of only positron emission tomography images, many experiments may be conducted at low costs for diagnosis of patients and research into patients.

In addition, since spatial normalization is performed using an individually adaptable optimal template instead of using a template obtained by using average data in the related art, various features of PET images of individuals may be accurately reflected in the spatial normalization.

BRIEF DESCRIPTION OF DRAWINGS

FIG. 4 is a flowchart illustrating a process for spatially normalizing a medical image according to an embodiment of the present invention.

BEST MODE

Figure 1:
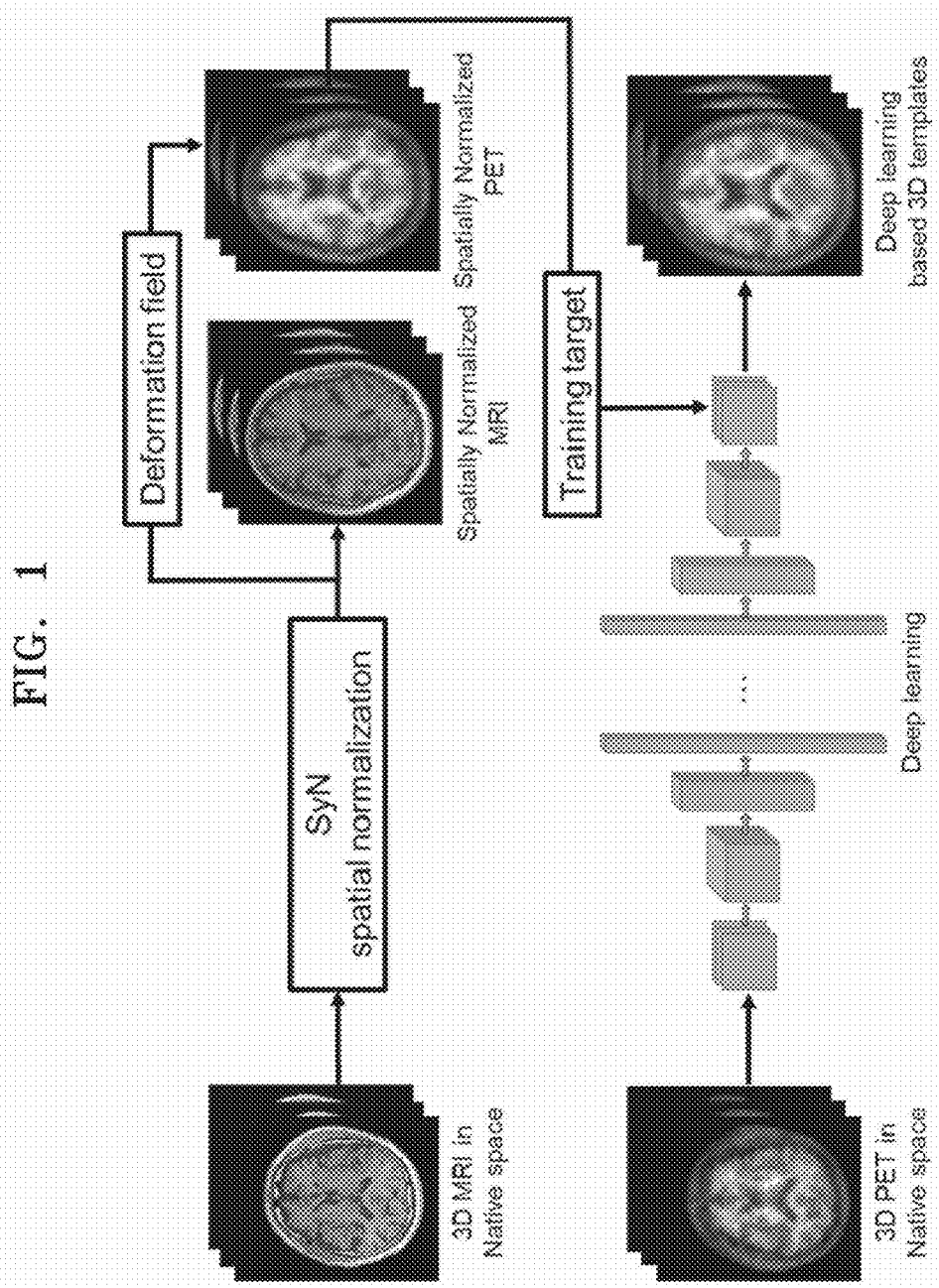
FIG. 1 is a flowchart illustrating a process for spatial normalization of a medical image according to an embodiment of the present invention.

Embodiments of the present invention will now be described in detail with reference to the accompanying drawings so that those of ordinary skill in the art may easily implement the present invention. However, the present invention may be implemented in various other ways and is not limited to the embodiments described herein. In the drawings, portions not relevant to the present invention may be omitted for clarity of illustration, and the same or similar elements are denoted with the same reference numerals throughout the specification. In addition, detailed descriptions of well-known techniques are omitted.

In the specification, it will be further understood that the terms "including" and/or "comprising" specify the presence of stated features or elements, but do not preclude the presence or addition of one or more other features or elements.

Hereinafter, the overall flow for spatially normalizing a medical image through deep learning will be described in detail with reference to FIG. 1 according to an embodiment of the present invention.

FIG. 1 is a flowchart illustrating a process for spatially normalizing a medical image according to an embodiment of the present invention.

As shown in FIG. 1, in general, when a spatially normalized MRI image is generated through spatial normalization (SyN) of an MRI image (3D MRI image in a native space), a deformation field is extracted.

According to an embodiment of the present invention, a spatial normalization device 100 performs a deep learning process for a training target to produce a spatially normalized functional medical image (spatially normalized PET image) from a functional medical image (PET image) using the extracted deformation field.

In this manner, the spatial normalization device 100 may spatially normalize a functional medical image (PET image) through deep learning without 3D magnetic resonance imaging (MRI) or CT.

Hereinafter, functional medical images refer to, but are not limited to, images obtained by positron emission tomography (PET) for three-dimensionally displaying physiochemical and functional images of the human body using radiopharmaceuticals that emit positrons, and also refer to any other functional medical images such as SPECT, fMRI, EEG, or EMG images which are difficult to spatially normalize using independent information.

Hereinafter, the spatial normalization device 100, which is configured to spatially normalize a functional medical image (PET image) using a trained artificial neural network, will be described in detail with reference to FIG. 2.

Figure 2:
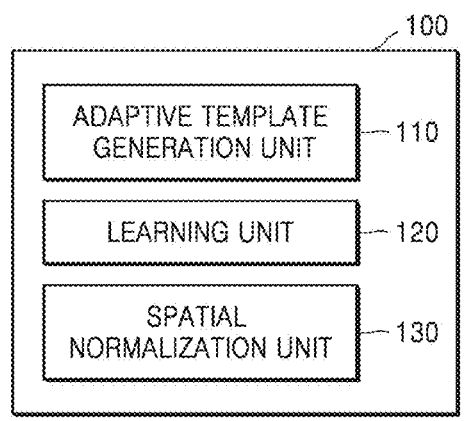
FIG. 2 is a view illustrating a configuration of a device for spatially normalizing a medical image through deep learning according to an embodiment of the present invention.
Figure 3A:
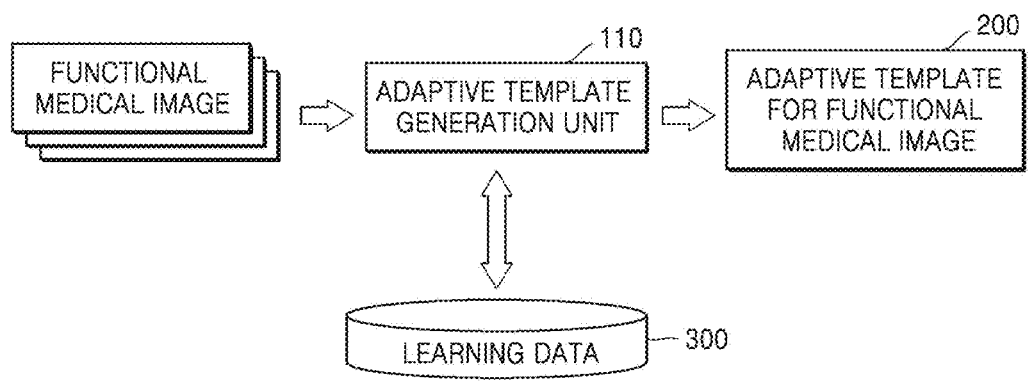
FIGS. 3A and 3B are example views illustrating an adaptive template generation unit and a learning unit according to an embodiment of the present invention.
Figure 3B:
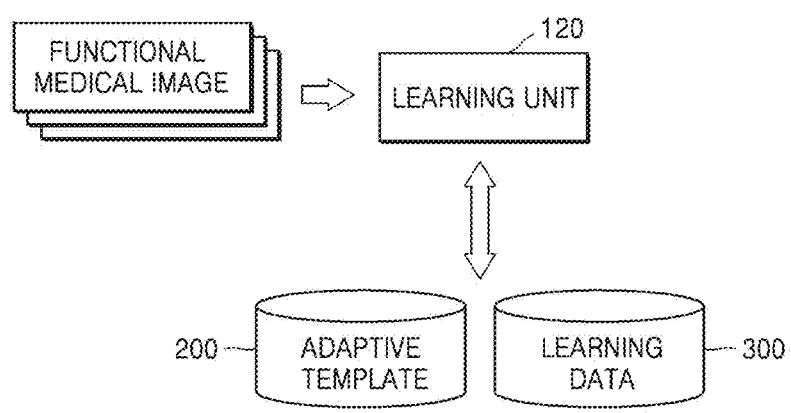

FIG. 2 is a view illustrating a spatial normalization device configuration for spatially normalizing a medical image through deep learning according to an embodiment of the present invention, and FIGS. 3A and 3B are views illustrating an adaptive template generation unit and a learning unit according to an embodiment of the present invention.

As shown in FIG. 2, the spatial normalization device 100 for spatially normalizing a medical image includes an adaptive template generation unit 110, a learning unit 120, and a spatial normalization unit 130.

First, the adaptive template generation unit 110 generates an adaptive template 200 for spatial normalization of a functional medical image.

When the adaptive template generation unit 110 receives a plurality of functional medical images, the adaptive template generation unit 110 inputs the functional medical images to a deep learning architecture (convolutional autoencoder: CAE) to generate, through deep learning, an adaptive template 200 which is individually adaptable.

In this case, as shown in FIG. 3A, the adaptive template generation unit 110 may perform deep learning by using prestored learning data 300.

Here, the prestored learning data 300 includes images spatially normalized based on magnetic resonance imaging (MRI).

In addition, the deep learning architecture includes a convolutional neural network and refers to an artificial neural network, which is capable of understanding an input image through calculation and obtaining information or generating a new image by extracting features from the input image.

Next, as shown in FIG. 3B, when the learning unit 120 receives a functional medical image of a user, the learning unit 120 generates a spatial normalized image using the adaptive template 200. In addition, the learning unit 120 determines authenticity based on the generated spatial normalized image and the prestored learning data.

In other words, when the learning unit 120 receives a functional medical image of a user, the learning unit 120 performs iterative learning on the functional medical image of the user through a generative adversarial network (GAN).

Here, the generative adversarial network (GAN) refers to a machine learning network for generating an image similar to the original data distribution, and is used as a technique for easily and quickly creating a fake which looks like real. The generative adversarial network (GAN) learns and derives results through competition between two neural network models: a generator (G) and a discriminator (D). The generator (G) learns real data to generate data that is similar to real data, and generates data based on the learning, and the discriminator (D) learns to determine whether the data generated by the generator (G) is real or false.

The learning unit 120 repeats a process of generating a spatial normalized image based on the received functional medical image of the user by using the generative adversarial network, and determining the authenticity of the generated image. Through this iterative learning, the learning unit 120 may derive results very similar to results of spatial normalization of the functional medical image which is performed using an image obtained by performing spatial normalization based on magnetic resonance imaging (MRI).

The learning unit 120 sequentially repeats a process of generating an image by spatially normalizing the functional medical image of the user and determining the authenticity of the generated image until the generated spatially normalized image is not distinguishable from prestored data.

Next, the spatial normalization unit 130 spatially normalizes the functional medical image of the user through the generative adversarial network which finished learning. In addition, the spatial normalization unit 130 provides the spatially normalized functional medical image of the user.

In addition, the spatial normalization device 100 for spatially normalizing a medical image may be a server, a terminal, or a combination thereof.

The terminal refers to any device including a memory and a processor to have a calculation ability. Examples of the terminal include personal computers, handheld computers, personal digital assistants (PDAs), cellular phones, smart devices, tablets, and the like.

The server may include: a memory that stores a plurality of modules; a processor that is coupled to the memory, responses to the modules, and processes service information to be provided to the terminal or action information for controlling the service information; a communication unit; and a user interface (UI) display unit.

The memory is a device for storing information, and examples of the memory include various memories such as high-speed random access memories, magnetic disk storage devices, flash memory devices, and other non-volatile memories such as non-volatile solid-state memory devices.

The communication unit transmits and receives service information or action information to and from the terminal in real time.

The UI display unit outputs service information or action information of the device in real time. The UI display unit may be an independent device that directly or indirectly outputs or displays a UI, or may be part of the device.

Hereinafter, a process in which the spatial normalization device 100 generates an adaptive template and a spatially normalized functional medical image using a generative adversarial network will be described in detail with reference to FIGS. 4, 5A, and 5B.

Figure 5A:
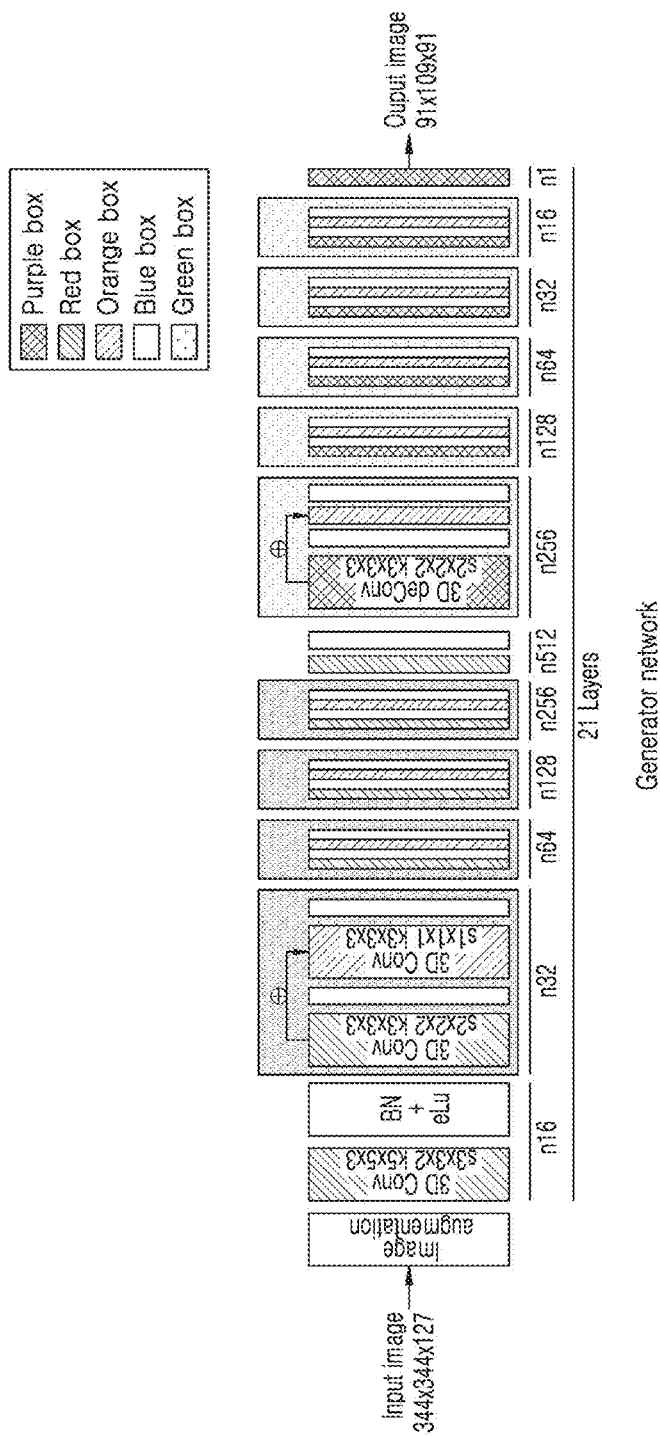
FIGS. 5A and 5B are example views illustrating a deep learning architecture and a generative adversarial network according to an embodiment of the present invention.
Figure 5B:
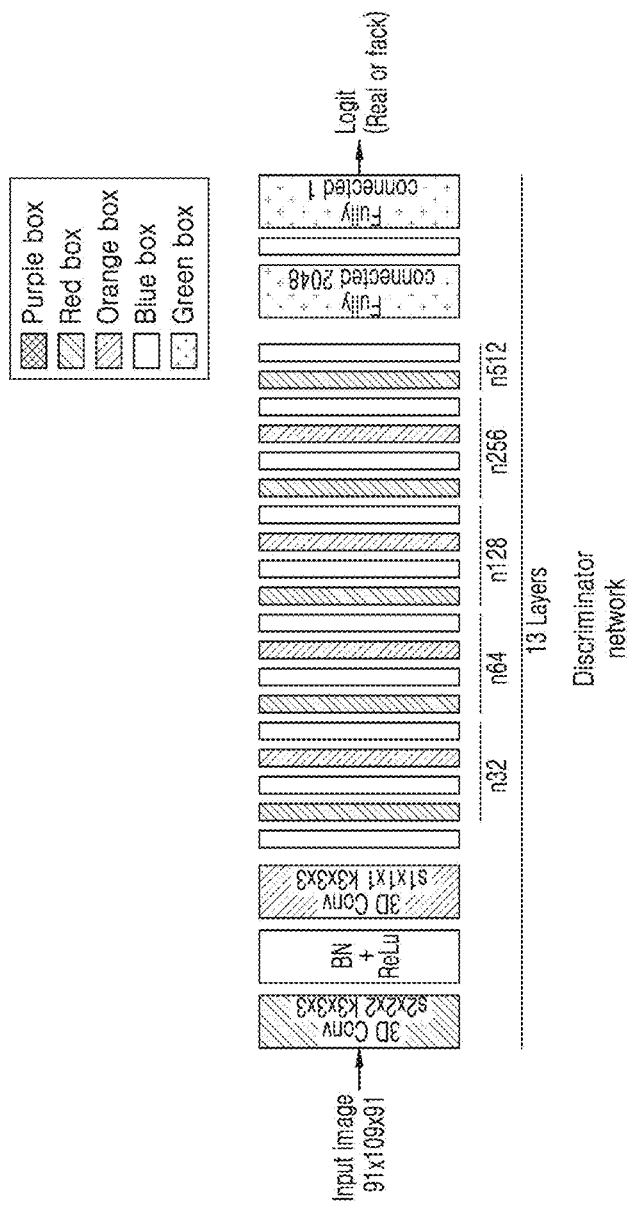

FIG. 4 is a flowchart illustrating a process of spatially normalizing a medical image according to an embodiment of the present invention, and FIGS. 5A and 5B are example views illustrating a deep learning architecture and a generative adversarial network according to an embodiment of the present invention.

As shown in FIG. 4, the spatial normalization device 100 generates an adaptive template by inputting a plurality of functional medical images corresponding to various environments into a deep learning architecture (S410).

Here, the deep learning architecture (CAE) includes a plurality of layers, and all convolutional layers thereof extract features by a 3D method. In addition, the deep learning architecture (CAE) performs calculation by strided convolution and applies an exponential linear unit (ELU) activation function after the convolution.

In addition, batch normalization is applied to the deep learning architecture (CAE) except for the final output layer.

The spatial normalization device 100 may measure a difference between an adaptive template result derived through the deep learning architecture and a prestored MRI-based spatial normalization result.

In other words, during a process of measuring a difference between a value output from the deep learning architecture and a prestored MRI-based spatial normalization result, the spatial normalization device 100 performs deep learning in such a manner that a loss function (LCAE) expressed by Condition 1 below is minimized.

$$L_{CAE} = \frac{1}{m}\sum_{i=1}^{m} \frac{(I_i^{MNI} - CAE(I_i^{Native}))^2}{N} \quad \text{[Condition 1]}$$

where m refers to a batch size, $1_i^{MNI}$ refers to an MRI-based spatial normalization (label) image in an MNI space, $1_i^{Native}$ refers to an input functional medical image of a user in a basic space, and N refers to the number of voxels in the MNI space.

As described above, the spatial normalization device 100 may generate an adaptive template capable of individually performing spatial normalization through deep learning of the deep learning architecture (CAE).

Next, the spatial normalization device 100 receives a functional medical image of a user (S420).

The spatial normalization device 100 may receive the functional medical image of the user from a user terminal (not shown) or a server (not shown) that interacts with the spatial normalization device 100 through any communication network for data transmission, such as a wired communication network, a short-range or remote wireless communication network, or a combination thereof.

In addition, the spatial normalization device 100 repeats learning while generating an image by applying the functional medical image of the user to the adaptive template and determining the authenticity of the generated image (S430).

The spatial normalization device 100 may perform learning while sequentially updating a generation model and a distinction model through the generative adversarial network (GAN).

First, the spatial normalization device 100 spatially normalizes the functional medical image of the user based on the adaptive template by using a generator (G) of the generative adversarial network (GAN), and generates a spatially normalized image.

In addition, the spatial normalization device 100 may determine authenticity by comparing the spatially normalized image with an MRI-based spatially normalized image, which is prestored learning data, by using a discriminator (D) of the generative adversarial network (GAN).

FIG. 5A is an example view illustrating a network structure of the generator (G) of the generative adversarial network (GAN), and FIG. 5B is an example view illustrating a network structure of the discriminator (D) of the generative adversarial network (GAN).

Referring to FIGS. 5A and 5B, each red box and each orange box refer to 3D strided convolutional kernels, s refers to a stride size, and k refers to a kernel size. Each blue box refers to batch normalization combined with an activation function such as a leak-ReLU or ELU. In addition, each green box refers to a layer fully connected to the number of devices, and each purple box refers to a 3D deconvolution layer with two strides and a kernel size of 3.

In addition, as shown in FIG. 5A, the generator (G) of the generative adversarial network (GAN) may be used as the same neural network as the deep learning architecture (CAE), but is not limited thereto.

The spatial normalization device 100 uses the generator (G) and the discriminator (D) of the generative adversarial network (GAN) to sequentially repeat generating a spatially normalized image when the discriminator (D) generates a determination result value, and performing determination.

The spatial normalization device 100 is trained as the generative adversarial network (GAN) solves a min-max problem such as Condition 2 below.

$$\min_{\theta_G}\max_{\theta_D} E_{x\sim Pdata(x)}[\log D(x)] + E_{z\sim PG(z)}[1 - \log D(G(z))] \quad \text{[Condition 2]}$$

where z refers to a PET image in a native space (input), x refers to an MRI-based spatial normalization result (label), $\theta_G$ and $\theta_D$ respectively refer to a generator parameter and a discriminator parameter, and E refers to an expected value for a given probability distribution.

First, max D refers to finding a discriminator (D) that maximizes an objective function.

In Condition 2, the first term E[Log D(x)] refers to the value of the objective function which is the result of MRI-based spatial normalization (x). In addition, the second term E[log(1−D(G(z)))] has an image (G(z)) generated by the generator, and since the inside of the second term is 1−log D(G(z)) for arg max D, the maximization of the second term means the minimization of D(G(z)).

As a result, the spatial normalization device 100 trains the discriminator (D) such that the discriminator (D) may output a large value in response to an input real image and a low value in response to an input fake image by using the objective function of two terms.

Next, min G refers to finding a generator (G) that minimizes the objective function.

In Condition 2, G is included only in the second term, and when G minimizes the entire function, G minimizes the second term and eventually maximizes D(G(z)).

As a result, assuming an optimal discriminator (D), the objective function for the generator (G) is the same as minimizing a Jensen-Shannon divergence between D(x) and D(G(z)).

Therefore, the spatial normalization device 100 may repeatedly learn and update the generator (G) and the discriminator (D) to minimize the Jansen-Shannon divergence between the data probability distribution of a spatially normalized image and the data probability distribution of normalized MRI.

In addition, as shown in Condition 3 below, the spatial normalization device 100 may add fidelity loss between images generated by the generator (G) and MRI-based spatial normalization results (labels) to the min-max problem.

$$\min_{\theta_G}\max_{\theta_D} E_{x\sim Pdata(x)}[\log D(x)] + \quad \text{[Condition 3]}$$
$$E_{z\sim PG(z)}[1 - \log D(G(z))] + 10^{-5} L_{GAN}^{fid}$$

where $$L_{GAN}^{fid} = \sum_{i=0}^{m} \frac{(I_i^{MNI} - G(Z_i))^2}{\sum_{all\ voxels} I_i^{MNI}}$$

where D( ) refers to a generator which generates an image, G( ) refers to a discriminator which determines an image, z refers to a functional medical image in a native space, x refers to MRI-based SN results, $\theta_G$ and $\theta_D$ respectively refer to a parameter of the generator and a parameter of the discriminator, E refers to an expected value for a given probability distribution, $L_{GAN}^{fid}$ refers to fidelity loss between MRI-based SN results, m refers to a batch size, refers to an image indicating MRI-based SN results in an MNI space, and refers to a functional medical image in a basic space.

As described above, the generator (G), which is repeatedly trained, may generate an image by spatially normalizing a functional medical image of a user which is very similar to MRI-based spatial normalization results.

In this process, when the discriminator (D) of the generative adversarial network (GAN) is not able to distinguish between MRI-based spatial normalization results and the spatially normalized image generated by the generator (G), the spatial normalization device 100 finishes the corresponding learning.

Next, the spatial normalization device 100 provides a spatially normalized medical image by spatially normalizing the functional medical image of the user through a learned algorithm (S440).

The spatial normalization device 100 may spatially normalize the functional medical image of the user through the generator (G) of the generative adversarial network (GAN) which has finished learning, and may provide the spatially normalized functional medical image.

In addition, the spatial normalization device 100 may provide a spatially normalized functional medical image to which the adaptive template generated in operation S410 is applied. In other words, the spatial normalization device 100 may generate only an adaptive template 200 using the deep learning architecture (CAE), spatially normalize a functional medical image by using only the adaptive template 200, and provide the spatially normalized functional medical image.

Hereinafter, with reference to FIGS. 6 and 7, a method of spatially normalizing a medical image according to an embodiment of the present invention will be compared with a spatial normalization method using an average template, and accuracy relative to MRI information will be described in detail.

Figure 6:
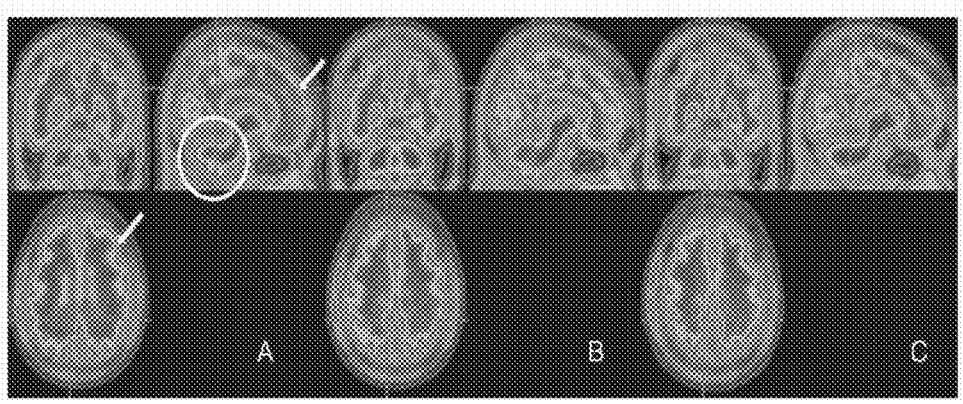
FIG. 6 is a view for comparing images spatially normalized by a method according to an embodiment of the present invention, an average template method, and a method using magnetic resonance image information.
Figure 7:
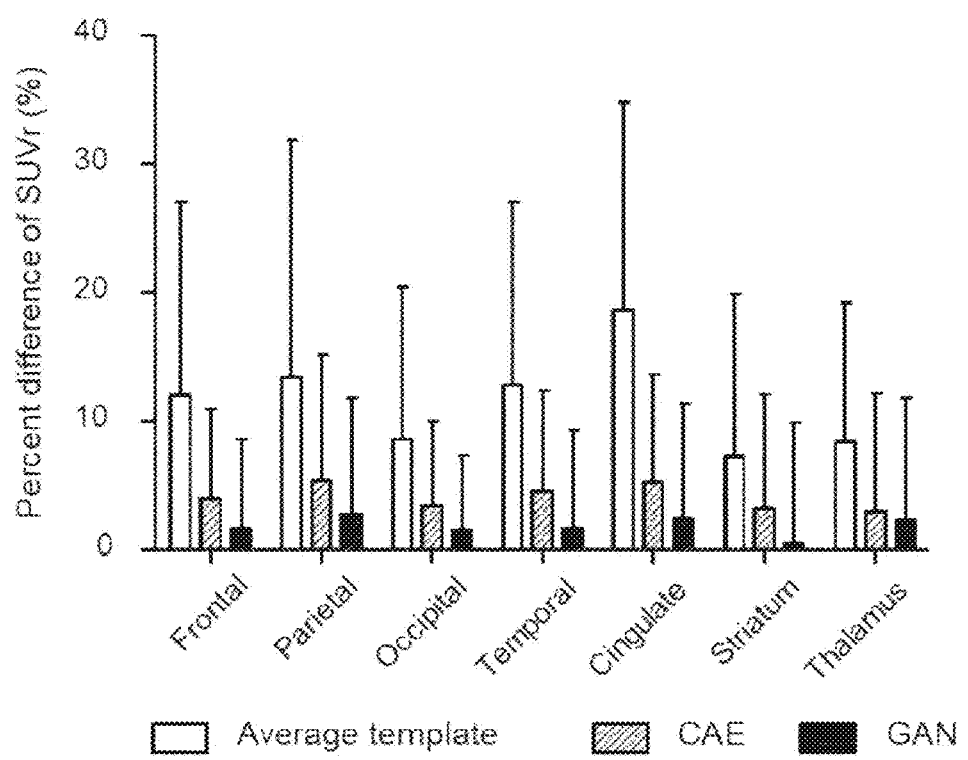
FIG. 7 is view illustrating standardized uptake value ratios in a method according to an embodiment of the present invention and a method using magnetic resonance image information and standardized uptake value ratios in an average template method and a method using magnetic resonance image information.

FIG. 6 is a view for comparing images spatially normalized by a method according to an embodiment of the present invention, an average template method, and a method using magnetic resonance image information, and FIG. 7 is view illustrating standardized uptake value ratios in a method according to an embodiment of the present invention and a method using magnetic resonance image information and standardized uptake value ratios in an average template method and a method using magnetic resonance image information.

Region A of FIG. 6 shows a PET image spatially normalized using an average template, Region B of FIG. 6 shows a PET image spatially normalized by a method of the present invention, and Region C of FIG. 6 shows a PET image spatially normalized by a method using magnetic resonance image information.

Referring to FIG. 6, the images in Regions B and C are almost identical, but the image in Region A of FIG. 6 is different in portions indicated by arrows and a circle. In other words, a PET image spatially normalized using an average template has poor accuracy, but a PET image spatially normalized by a deep learning method proposed in the present invention has high accuracy.

FIG. 7 shows results of quantitative analysis of a spatial normalization method according to an embodiment of the present invention and a spatial normalization method using an average template.

FIG. 7 is a graph illustrating standardized uptake value ratios (SUVr) for comparison of errors relative to MRI information in selected regions of the brain.

Referring to FIG. 7, results (white blocks) of spatial normalization using an average template have errors of up to about 20%, distinction models (hatched blocks) using the deep learning architecture (convolutional auto-encoder: CAE) of the present invention have errors of less than 5%. In particular, the generative adversarial network (GAN) proposed in the present invention has the lowest errors.

Therefore, it can be understood that the method of the present invention, in which an adaptive template is generated using a deep learning architecture and a functional medical image is spatially normalized using the adaptive template through a generative adversarial network, shows results similar to those of a spatial normalization method using real MRI information.

Programs for executing the method of the embodiment of the present invention may be stored in computer-readable recording media.

The computer-readable recording media may include, individually or in combination, program instructions, data files, data structures, etc. The media may be those specially designed and configured or those well known to a person of ordinary skill in the computer software industry. The computer-readable recording media include hardware specifically configured to store program instructions and execute the program instructions, and examples of the hardware include: magnetic media such as hard disks, floppy disks, and magnetic tapes; optical media such as CD-ROMs and DVDs; magneto-optical media such as floptical disks; and ROMs, RAMs, and flash memories. Here, the media may include transmission media, such as light including carrier waves, metal wires, and waveguides, for transmitting signals such as program instructions and data structures. Examples of the program instructions may include not only a machine language code such as those generated by a compiler but also a high-level language code executable on a computer using an interpreter, etc.

While preferred embodiments of the present invention have been described in detail, the scope of the present invention is not limited thereto, and it will be understood by those of ordinary skill in the art that various modifications or improvements may be made therein without departing from the spirit and scope of the present invention as defined by the following claims.

| 100: device for spatially normalizing a medical image | 110: adaptive template generation unit |
|---|---|
| 120: learning unit | 130: spatial normalization unit |
| 200: adaptive template | 300: training data |

The invention claimed is:

1. A device for spatially normalizing a medical image, the device comprising:
a memory configured to store information; and
a processor coupled to the memory and configured to:
generate an adaptive template for spatially normalizing the plurality of functional medical images by inputting a plurality of functional medical images to a convolutional neural network;
learn by repeating a process of generating an image from an input functional medical image of a user based on the adaptive template through a generative adversarial network (GAN) and determining authenticity of the generated image;
provide the functional medical image of the user which is spatially normalized based on results of the learning;
generate a spatially normalized image by spatially normalizing the functional medical image of the user based on the adaptive template;
determine authenticity of the spatially normalized image by comparing the spatially normalized image with an image spatially normalized based on magnetic resonance imaging (MRI) data which is the prestored learning data, and after generating results of the determining, repeat a process of generating and determining a spatially normalized image; and
finish the learning when results of the determining show that the spatially normalized image is not distinguishable from the image spatially normalized based on the magnetic resonance imaging (MRI) data which is the prestored learning data,
wherein the convolutional neural network includes a plurality of layers and apply batch normalization to the plurality of layers except for a final output layer.

2. The device of claim 1, wherein the processor further configured to: be repeatedly trained to minimize a Jensen-Shannon divergence between a data probability distribution of the spatially normalized image and a data probability distribution of normalized magnetic resonance imaging (MRI).

3. The device of claim 1, wherein the processor further configured to: repeatedly learn through a process of solving a min-max problem using the following expression:

$$\min_{\theta_G}\max_{\theta_D} E_{x\sim Pdata(x)}[\log D(x)] + E_{z\sim PG(z)}[1 - \log D(G(z))] + 10^{-5} L_{GAN}^{fid}$$

where $$L_{GAN}^{fid} = \sum_{i=0}^{m} \frac{(I_i^{MNI} - G(Z_i))^2}{\sum_{all\ voxels} I_i^{MNI}}$$

where D( ) refers to a generator which generates an image, G( ) refers to a discriminator which determines an image, z refers to a functional medical image in a native space, x refers to magnetic resonance imaging (MRI)-based SN results, $\theta_G$ and $\theta_D$ respectively refer to a parameter of the generator and a parameter of the discriminator, E refers to an expected value for a given probability distribution, $L_{GAN}^{fid}$ refers to fidelity loss between magnetic resonance imaging (MRI)-based SN results, m refers to a batch size, refers to an image indicating magnetic resonance imaging (MRI)-based SN results in an MNI space, and refers to a functional medical image in a basic space.

4. A method used by a device for spatially normalizing a medical image, the method comprising: generating an adaptive template for spatially normalizing the plurality of functional medical images by inputting a plurality of functional medical images to a convolutional neural network;

learning by repeating a process of generating an image from an input functional medical image of a user based on the adaptive template through a generative adversarial network (GAN) and determining authenticity of the generated image; and after the learning, providing a spatially normalized functional medical image of the user based on results of the learning;

wherein the convolutional neural network includes a plurality of layers and apply batch normalization to the plurality of layers except for a final output layer, wherein the learning comprises:

generating a spatially normalized image by spatially normalizing the functional medical image of the user based on the adaptive template;

determining authenticity of the spatially normalized image by comparing the spatially normalized image with an image spatially normalized based on magnetic resonance imaging (MRI) data which is prestored learning data;

when results of the determining are generated, sequentially repeating a process of generating a spatially normalized image and determining the spatially normalized image; and finishing the learning when results of the determining show that the spatially normalized image is not distinguishable from the image spatially normalized based on the magnetic resonance imaging (MRI) data which is prestored learning data.

5. The method of claim 4, wherein the sequential repeating comprises iterative learning for minimizing a Jensen-Shannon divergence between a data probability distribution of the spatially normalized image and a data probability distribution of normalized magnetic resonance imaging (MRI).

6. The method of claim 4, wherein the learning comprises iterative learning through a process of solving a min-max problem using the following expression:

$$\min_{\theta_G}\max_{\theta_D} E_{x\sim Pdata(x)}[\log D(x)] + E_{z\sim PG(z)}[1 - \log D(G(z))] + 10^{-5} L_{GAN}^{fid}$$

where $$L_{GAN}^{fid} = \sum_{i=0}^{m} \frac{(I_i^{MNI} - G(Z_i))^2}{\sum_{all\ voxels} I_i^{MNI}}$$

where D( ) refers to a generator which generates an image, G( ) refers to a discriminator which determines an image, z refers to a functional medical image in a native space, x refers to magnetic resonance imaging (MRI)-based SN results, $\theta_G$ and $\theta_D$ respectively refer to a parameter of the generator and a parameter of the discriminator, E refers to an expected value for a given probability distribution, $L_{GAN}^{fid}$ refers to fidelity loss between magnetic resonance imaging (MRI)-based SN results, m refers to a batch size, refers to an image indicating magnetic resonance imaging (MRI)-based SN results in an MNI space, and refers to a functional medical image in a basic space.

\* \* \* \* \*